(12) United States Patent
Kamal et al.

(10) Patent No.: US 8,394,954 B2
(45) Date of Patent: Mar. 12, 2013

(54) BENZOPHENONE HYBRIDS AS ANTICANCER AGENTS AND PROCESSES FOR THE PREPARATION THEREOF

(75) Inventors: Ahmed Kamal, Hyderabad (IN); Bandari Rajendra Prasad, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 532 days.

(21) Appl. No.: 12/594,102

(22) PCT Filed: Mar. 26, 2008

(86) PCT No.: PCT/IN2008/000192
§ 371 (c)(1), (2), (4) Date: Feb. 22, 2010

(87) PCT Pub. No.: WO2008/120235
PCT Pub. Date: Oct. 9, 2008

(65) Prior Publication Data
US 2010/0174074 A1 Jul. 8, 2010

(30) Foreign Application Priority Data

Mar. 30, 2007 (IN) .............................. 698/DEL/2007

(51) Int. Cl.
*C07D 239/04* (2006.01)
*C07D 241/04* (2006.01)
*C07D 295/00* (2006.01)

(52) U.S. Cl. ........ 544/293; 544/295; 544/360; 544/362; 544/376; 544/393; 544/397

(58) Field of Classification Search .................. 544/293, 544/295, 360, 362, 376, 393, 397
See application file for complete search history.

(56) References Cited

FOREIGN PATENT DOCUMENTS

| WO | WO 2006/088193 | * | 2/2006 |
| WO | 2006/088193 | | 8/2006 |

OTHER PUBLICATIONS

Hong, et al., Effects of Garcinol and Its Derivatives on Intestinal Cell Growth: Inhibitory Effects and Autoxidation-dependent Growth-stimulatory Effects, Free Radical Biology & Medicine, 42, 1211-1221 (2007).*

* cited by examiner

*Primary Examiner* — Erich A Leeser
(74) *Attorney, Agent, or Firm* — K&L Gates LLP

(57) ABSTRACT

Disclosed herein are benzophenone hybrids with potent anti-cancer activities and processes for creation of the same.

9 Claims, No Drawings

BENZOPHENONE HYBRIDS AS ANTICANCER AGENTS AND PROCESSES FOR THE PREPARATION THEREOF

CROSS-REFERENCE TO RELATED APPLICATIONS

This application claims the benefit under 35 U.S.C. §371 of International Patent Application PCT/IN2008/000192 filed Mar. 26, 2008, and also claims the benefit of Indian Patent Application 698/DEL/2007 filed Mar. 30, 2007 in India. The entire disclosures of both applications are incorporated by reference herein.

BACKGROUND

In the last few years, a growing interest has been shown in the development of new benzophenone hybrids with potent anticancer activities.

SUMMARY

Benzophenone-type ca-4 analogues are attractive targets for anti-tubulin agents, as the benzophenone backbone not only provides ease of synthesis without the need to control the geometric selectivity (z and e geometry) but also increases the pharmacological potential through increased drug stability and water solubility.

Some example embodiments disclosed herein include a series of benzophenone-type analogues of combretastatin A-4. Some of the compounds are potent antiproliferative agents, inhibitors of tubulin polymerization, and inhibitors of colchicine binding to tubulin. In addition, these compounds cause G2/M phase arrest of cells and are considered to be potential new antimitotic agents for clinical use. The lead compounds most likely interact with tubulin at the colchicine site and display potent growth inhibitory activity against human cancer cells, including multi-drug resistant cancer cells. Most significantly, compounds 6c, 6d and 8a described below showed a 10- to 100-fold increase in growth inhibition compared to both phenstatin and combretastatin A-4 against several human cancer cell lines. Examination of the SAR in this series of benzophenone-type analogues revealed that introduction of an amido group at the ortho position plays a significant role in increased growth inhibition.

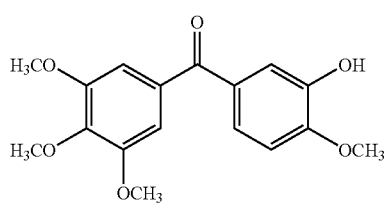

phenstatin

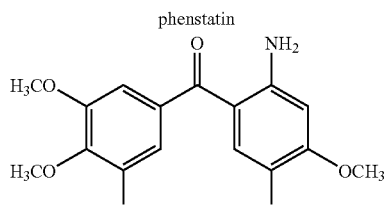

2-Amino benzophenone

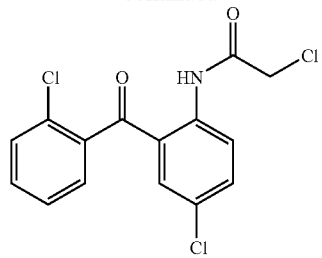

Amido benzophenone

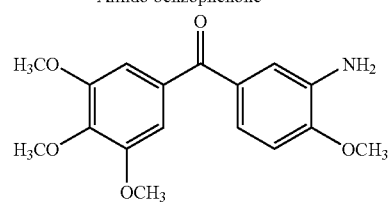

3-Amino benzophenone

One objective of some of the example embodiments disclosed herein is to provide benzophenone hybrids of formula A useful as antitumor agents.

Another objective of some of the example embodiments disclosed herein is to provide a process for the preparation of benzophenone hybrids.

Formula A

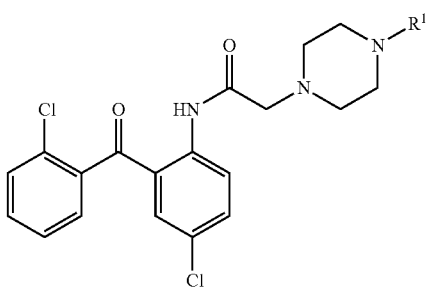

$R^1$ = pyridyl, pyrimidyl, 2-methoxy phenyl, quinazolinyl, butyl chalcone,

Accordingly, some example embodiments disclosed herein provide benzophenone hybrids of formula A as potential anticancer agents wherein R1 is elected from the group consisting of pyridyl, pyrimidyl, 2-methoxy piperazine, 4-chloroquinazoline, 2-(tert-butyl)imidazo[1,2-a]pyridine-8-carbonyl, N1-[4-chloro-2-(2-chlorobenzoyl)phenyl]-2-chloro acetamide, 1,3-dibromo propane) and butyl chalcone.

In some alternative example embodiments the representative compounds of the benzophenone hybrids of formula A include, without limitation:

N1-[4-chloro-2-(2-chlorobenzoyl)phenyl]-2-[4-(2-pyridyl)piperazino]acetamide (6a);

N1-[4-chloro-2-(2-chlorobenzoyl)phenyl]-2-[4-(2-pyrimidinyl)piperazino]acetamide (6b);

N1-[4-chloro-2-(2-chlorobenzoyl)phenyl]-2-[4-(2-methoxyphenyl)piperazino]acetamide (6c);

N1-4-chloro-2-(2-chlorobenzoyl)phenyl]-2-[4-(4-quinazolinyl)piperazino]acetamide (6d);

N1-[4-chloro-2-(2-chlorobenzoyl)phenyl]-2-(4-[2-(tert-butyl)imidazo[1,2-a]pyridin-8-yl]carbonylpiperazino)acetamide (6e);

N1-[4-chloro-2-(2-chlorobenzoyl)phenyl]-2-(4-2-[4-chloro-2-(2-chloro benzoyl)anilino]-2-oxoethylpiperazino)acetamide (6f);

N1-[4-chloro-2-(2-chlorobenzoyl)phenyl]-2-4-[3-(4-2-[4-chloro-2-(2-chlorobenzoyl)anilino]-2-oxoethylpiperazino)propyl]piperazino acetamide (6g)

N/1-[4-chloro-2-(2-chlorobenzoyl)phenyl]-2-[4-(4-4-[(E)-3-(4-fluorophenyl)-3-oxo-1-propenyl]-2-methoxyphenoxybutyl),piperazino]acetamide (6h);

N/1-[4-chloro-2-(2-chlorobenzoyl)phenyl]-2-(4-3-[(4-oxo-3-phenyl-4H-2-chromenyl)oxy]propylpiperazino)acetamide (8a) and 2-(4-4-[4-(2-benzoyl-4-chlorophenoxy)butyl]piperazinobutoxy)-5-chlorophenyl](Phenyl)methanone (8b).

In yet another example embodiment the general structure of the representative compounds of benzophenone hybrid of formula A are as follows:

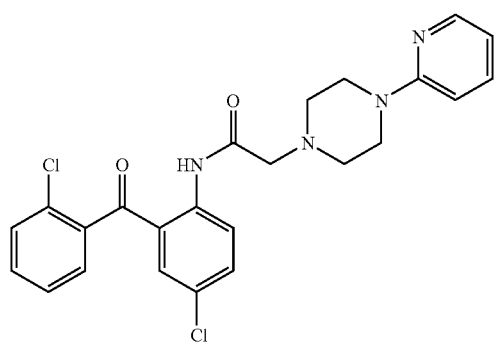

6a

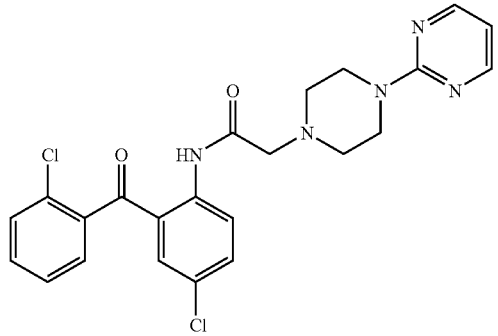

6b

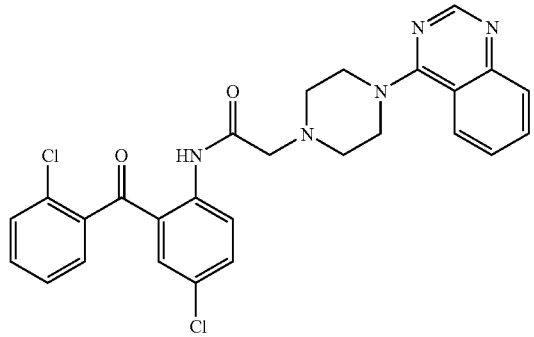

6d

6c

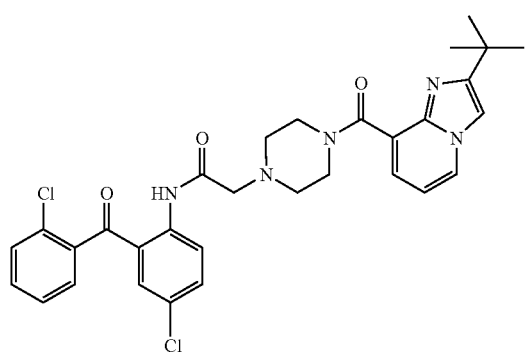

6e

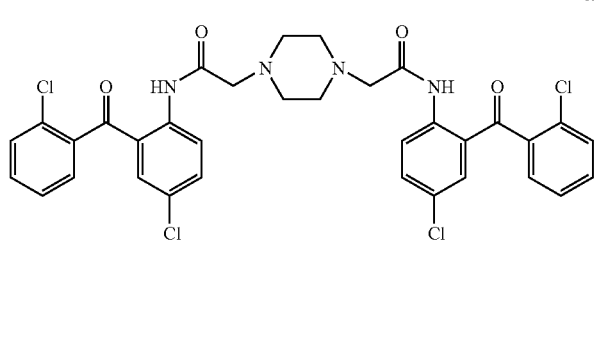

6f

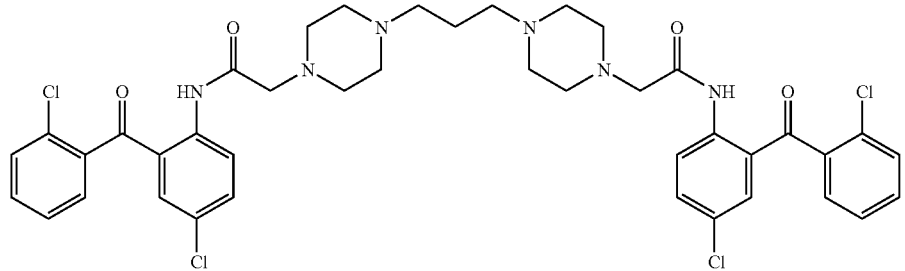

6g

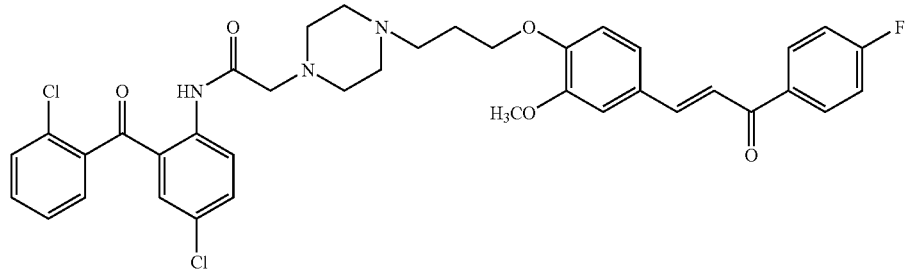

6h

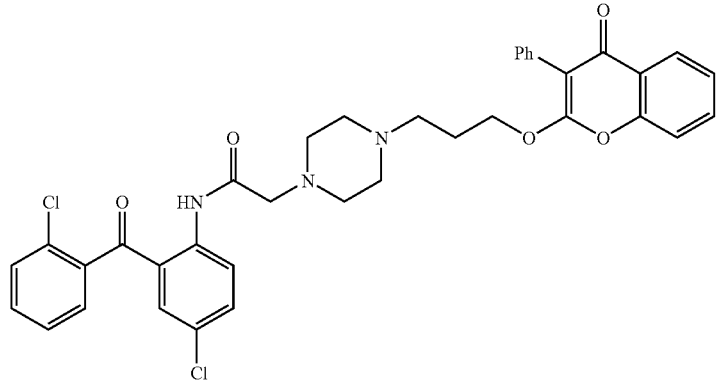

8a

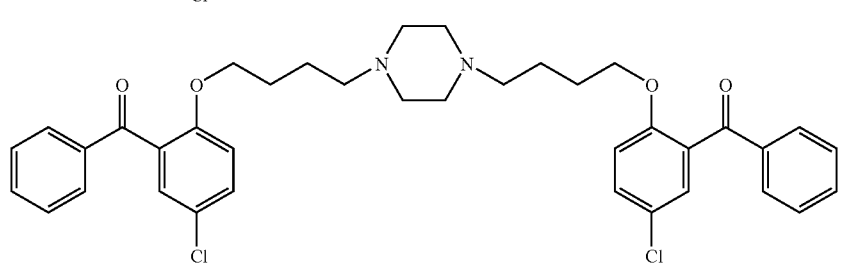

8b

In yet another example embodiment the benzophenone hybrids of formula A have the following characteristics with regards to thermal denaturation data of the benzophenone hybrids with calf thymus (CT) DNA:

| Compounds | [BPD]:[DNA] molar ratio[b] | $\Delta T_m$ (° C.)[a] after incubation at 37° C. for | | |
|---|---|---|---|---|
| | | 0 h | 18 h | 36 h |
| 6a | 1:5 | 1.2 | 1.7 | 2.2 |
| 6b | 1:5 | 1.5 | 2.1 | 2.6 |
| 6c | 1:5 | 1.4 | 1.6 | 2.3 |
| 6d | 1:5 | 1.5 | 1.9 | 2.7 |
| 6e | 1:5 | 1.9 | 2.3 | 2.8 |
| 6f | 1:5 | 1.3 | 2.1 | 3.0 |
| 6g | 1:5 | 1:6 | 2.6 | 2.9 |
| 8 | 1:5 | 1:5 | 2.3 | 2.4 |
| 8a | 1:5 | 1.4 | 2.1 | 2.1 |
| 8b | 1:5 | 1.6 | 2.6 | 2.9 |
| DC-81 | 1:5 | | 0.3 | 0.7 |

[a]For CT-DNA alone at pH 7.00 ± 0.01, $T_m$ = 69.6° C. ± 0.01 (mean value (Data from 10 separate determinations, all ΔTm values are ± 0.1-0.2° C.
[b] For a 1:5 molar ratio of [ligand]/[DNA], where CT-DNA concentration = 100 μM and ligand concentration = 20 μM in aqueous sodium phosphate buffer [10 mM sodium phosphate + 1 mM EDTA, pH 7.00 ± 0.01].
BPD = benzophenone derivatives.

In yet another example embodiment the benzophenone hybrids of formula A exhibit in vitro anticancer activity against human cell lines.

In yet another example embodiment the human cancer lines used are derived from the cancer type, selected from the group consisting of colon, leukemia, prostate, ovarian, lung, renal, CNS, melanoma and breast cancer.

In yet another example embodiment the compounds 6a-e and 8a-b exhibit log 10GI50 (50% cell growth inhibition) mean graphs mid point against human tumor cell lines in the range of about −5.5 to about −7.0.

In yet another example embodiment the compounds 6a-e and 8a-b exhibit log 10TGI (total cell growth inhibition) mean graphs mid point against human tumor cell lines in the range of about −5.5 to about −7.0.

In, yet another example embodiment the compounds 6a-e and 8a-b exhibit log 10LC50 (50% cell death) mean graphs mid point against human tumor cell lines in the range of about −4.0 to about −5.5.

In yet another example embodiment the compounds 6a-e and 8a-b exhibit log 100 GI50 (mol/L causing 50% growth inhibition) against human tumor cell lines in the range of about −5.0 to about −7.0.

Some example embodiments disclosed herein further provide a process for the preparation of benzophenone hybrids of formula A as potential anticancer agent

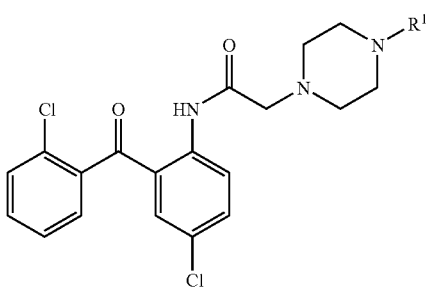

wherein R1 is elected from the group consisting of pyridyl, pyrimidyl, 2-methoxy piperazine, 4-chloroquinazoline, 2-(tert-butyl)imidazo[1,2-a]pyridine-8-carbonyl, N1-[4-chloro-2-(2-chlorobenzoyl)phenyl]-2-chloro acetamide, 1,3-dibromo propane) and butyl chalcone and the process comprises the steps of:

a) preparing a compound N1-[4-chloro-2-(2-chlorobenzoyl)phenyl]-2-chloroacetamide of formula 5 from a compound of formula 1,

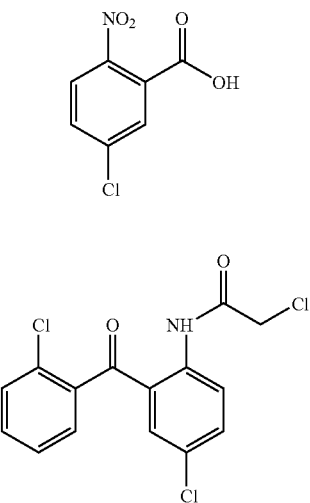

b) reacting the above compound N1-[4-chloro-2-(2-chloro benzoyl)phenyl]-2-chloroacetamide of formula 5 with anhydrous potassium carbonate and a reagent selected from the group consisting of (i) 1-(2-pyridyl)piperazine, (ii) 1-(2-pyrimidinyl)piperazine, (iii) 1-(2-methoxyphenyl)piperazine, (iv) 4-piperazinoquinazoline, (v) (tert-butyl) imidazo[1,2-a]pyridine-8-carbonyl chloride, (vi) N1-[4-chloro-2-(2-chlorobenzoyl)phenyl]-2-chloroacetamide, (vii) N1-[4-chloro-2-(2-chlorobenzoyl)phenyl]-2-piperazinoacetamide in acetone, under reflux, for a period of 0.20-30 hrs, followed by the removal of potassium carbonate by filtration and evaporating the solvent, under vacuum, and purifying the resultant product to obtain the desired corresponding compounds 6a-g of the general formula A, c) reacting the above N1-[4-chloro-2-(2-chloro benzoyl) phenyl]-2-chloroacetamide compound of formula 5 with Boc-piperazine in acetone under reflux for a period of about 15 to about 20 hrs, followed by the evaporation of solvent to obtain the compound of formula 6',

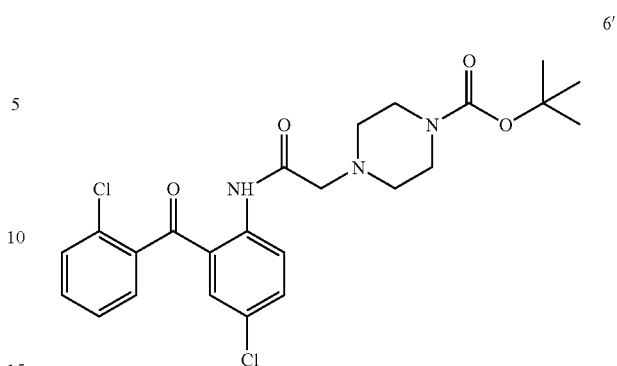

d) reacting the above said compound 6' obtained in step (c) with TFA (Trifluoroacetic acid) in dichloromethane, at a temperature of about 20 to about 30° C., followed by the evaporation of solvent to obtain the compound N1-[4-chloro-2-(2-chlorobenzoyl)phenyl]-2-piperazino acetamide of formula 7

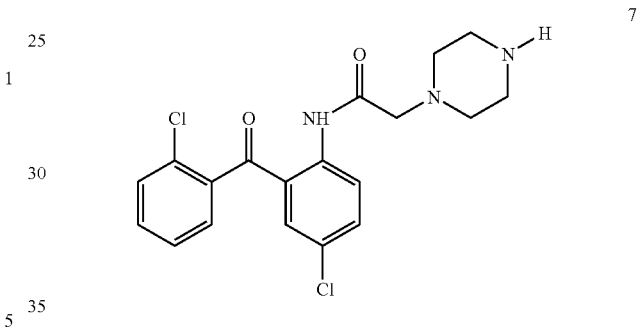

e) reacting the above said compound N1-[4-chloro-2-(2-chlorobenzoyl)phenyl]-2-piperazinoacetamide of formula 7 with (E)-3-{4-(3-bromopropoxy) 3-methoxyphenyl]-1-(4-fluorophenyl)-2-propen-1-one or 3-(3-bromopropoxy)-2-phenyl-4H-4-chromenone in acetone in the presence potassium carbonate, under reflux, for a period of about 15 to about 20 hrs, followed by the removal of potassium carbonate by filtration and evaporating the solvent, under vacuum, and purifying the resultant product to obtain the desired compound of N1-[4-chloro-2-(2-chlorobenzoyl)phenyl]-2-[4-(4-4-[(E)-3-(4-fluorophenyl)-3-oxo-1-propenyl]-2-methoxyphenoxy butyl)piperazino]acetamide or N1-[4-chloro-2-(2-chlorobenzoyl)phenyl]-2-(4-3-[(4-oxo-3-phenyl-4H-2-chromenyl)oxy]propylpiperazino)acetamide.

DETAILED DESCRIPTION

The described analogues of benzophenone hybrids linked with different precursor positions have shown promising DNA binding activity and efficient anticancer activity in various cell lines. The molecules synthesized are of immense biological significance with potential sequence selective DNA-binding properties. The following non-limiting steps/congeners were designed and synthesized:

1. The ether linkage at C-2 position of benzophenone intermediates with [2-(n-bromoalkyl)-5-chloropheny](phenyl) methanone moiety.
2. The amide linkage at C-2 position replace of chloro substituent with different substituents.
3. Refluxing the reaction mixtures for about 16 h.

4. Synthesis of novel benzophenone hybrids as antitumor antibiotics.

5. Purification by column chromatography using different solvents like, without limitation, ethyl acetate, hexane, dichloromethane and methanol.

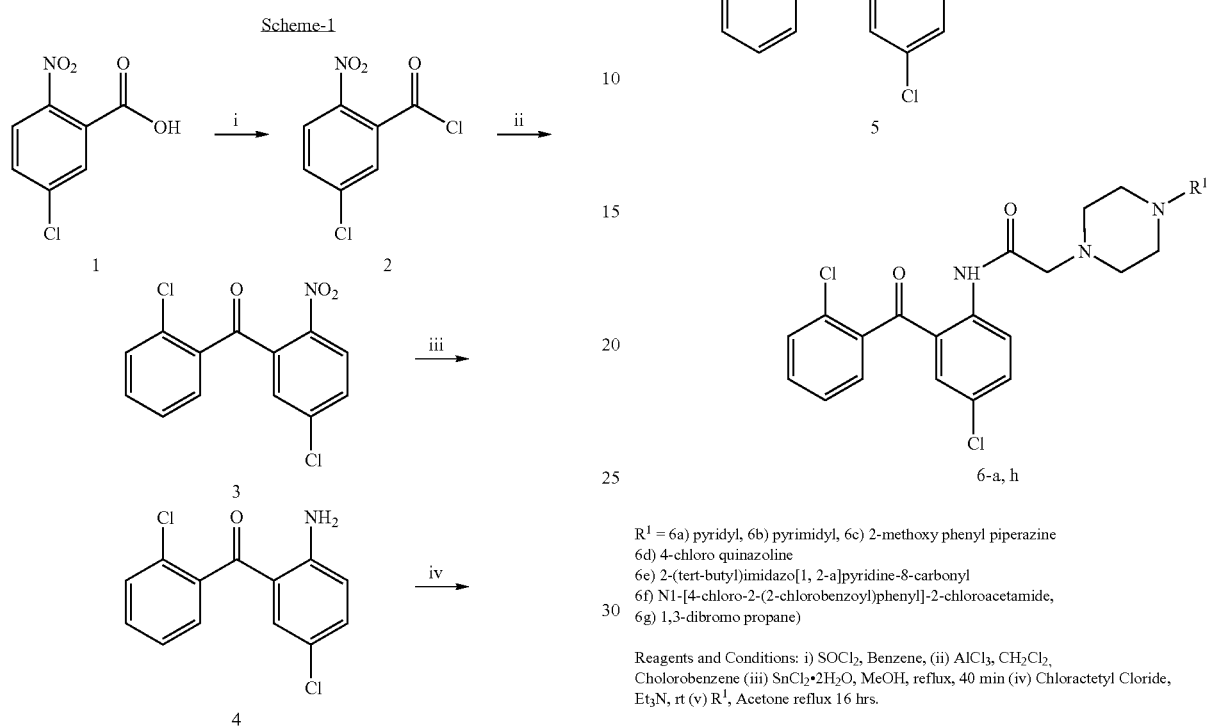

$R^1$ = 6a) pyridyl, 6b) pyrimidyl, 6c) 2-methoxy phenyl piperazine
6d) 4-chloro quinazoline
6e) 2-(tert-butyl)imidazo[1, 2-a]pyridine-8-carbonyl
6f) N1-[4-chloro-2-(2-chlorobenzoyl)phenyl]-2-chloroacetamide,
6g) 1,3-dibromo propane)

Reagents and Conditions: i) $SOCl_2$, Benzene, (ii) $AlCl_3$, $CH_2Cl_2$, Cholorobenzene (iii) $SnCl_2 \cdot 2H_2O$, MeOH, reflux, 40 min (iv) Chloractetyl Cloride, $Et_3N$, rt (v) $R^1$, Acetone reflux 16 hrs.

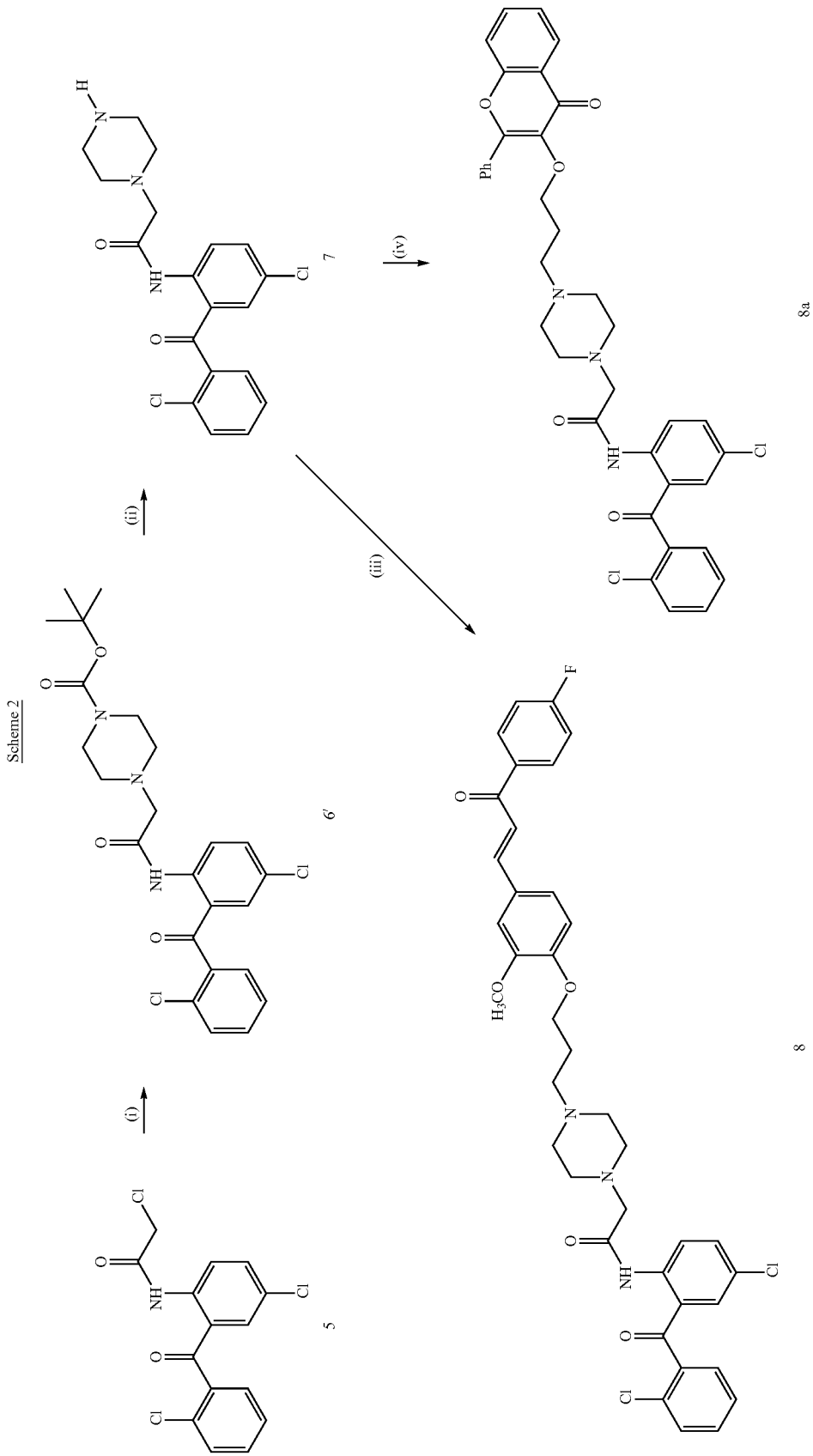

The following examples are given by way of illustration and therefore should not be construed to limit of the scope of exemplary embodiments disclosed herein.

Example 1

N1-[4-chloro-2-(2-chlorobenzoyl)phenyl]-2-[4-(2-methoxyphenyl)piperazino]acetamide (6c)

To a compound of N1-[4-chloro-2-(2-chlorobenzoyl)phenyl]-2-chloroacetamide (600 mg, 1.74 mmol) in dry acetone (20 mL) was added anhydrous potassium carbonate (1.21 g, 8.78 mmol) and 1-(2-methoxyphenyl)piperazine (336 mg, 1.98 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 6c (780 mg, 89% yield).

1H NMR (CDCl3); δ 2.0 (s, 2H), 2.78-2.90 (m, 4H), 3.20-3.35 (m, 4H), 3.80 (s, 3H) 6.80-7.00 (m, 4H), 7.20-7.60 (m, 6H), 8.80-8.90 (d, 1H J=9.06, Hz), 12.40 (s, 1H); FABMS: 498 (M+H);

Example 2

N1-[4-chloro-2-(2-chlorobenzoyl)phenyl]-2-[4-(2-pyridyl)piperazino]acetamide (6a)

To a compound of N1-[4-chloro-2-(2-chlorobenzoyl)phenyl]-2-chloroacetamide (500 mg, 1.46 mmol) in dry acetone (20 mL) was added anhydrous potassium carbonate (1 g, 7.30 mmol) and 1-(2-pyridyl)piperazine (238 mg, 1.46 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 6a (585 mg, 86% yield).

$^1$H NMR (CDCl$_3$) δ 2.70-2.82 (m, 4H), 3.21-3.24 (S, 2H), 3.70-3.80 (m, 4H), 6.54-6.62 (m, 2H), 7.20-7.56 (m, 7H), 8.10-8.14 (m, 1H), 8.80-8.12 (d, 2H J=9.06 Hz), 12.40 (s, 1H); FABMS: 469 (M+H).

Example 3

N1-[4-chloro-2-(2-chlorobenzoyl)phenyl]-2-[4-(2-pyrimidinyl)piperazino]acetamide (6b)

To a compound of N1-[4-chloro-2-(2-chlorobenzoyl)phenyl]-2-chloroacetamide (500 mg, 1.46 mmol) in dry acetone (20 mL) was added anhydrous potassium carbonate (1 g, 7.30 mmol) and 1-(2-pyrimidinyl)piperazine (239 mg, 1.46 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 6b (575 mg, 83% yield).

$^1$H NMR (CDCl$_3$) δ 2.68-2.72 (m, 4H), 3.40 (s, 2H)1 4.0-4.16 (m, 4H), 6.42-6.44 (d, 1H J=8.65 Hz), (7.25-7.80 (m, 6H)1 8.22-8.25 (d, 2H J=9.16 Hz), 8.80-8.92 (d, 2H J=9.06, Hz)1 12.40 (s, 1H); FABMS: 470 (M+H).

Example 4

N1-4-chloro-2-(2-chlorobenzoyl)phenylJ-2-[4-(4-quinazolinyl)piperazino]acetamide (6d)

To a compound of N1-[4-chloro-2-(2-chlorobenzoyl)phenyl]-2-chloroacetamide (500 mg, 1.46 mmol) in dry acetone (20 ml) was added anhydrous potassium carbonate (1 g, 7.30 mmol) and 4-piperazinoquinazoline (312 mg, 1.46 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 6d (672 mg, 89% yield).

1H NMR (CDCl3) δ 3.15-3.30, (m, 4H), 3.90 (s, 2H), 4.06-4.12 (m 4H)1 6.75 (, 1H), 7.20-7.65, (m, 10H), 8.90-8.95 (d, 1H J=9.06, Hz)1 12.40, (s, 1H); FABMS: 520 (M+H).

Example 5

N1-[4-chloro-2-chlorobenzoyl)phenyl]-2-[4-4-[(E)-3-(4-fluorophenyl)-3-oxo-1-propenyl]-2-methoxyphenoxybutyl)piperazino]acetamide (8)

To a compound of N1-[4-chloro-2-(2-chlorobenzoyl)phenyl]-2-piperazino acetamide (500 mg, 1.27 mmol) in dry acetone (20 mL) was added anhydrous potassium carbonate 880 mg, 6.37 mmol) and (E)-3-[4-(3-bromopropoxy)-3-methoxyphenyl]-1-(4-luorophenyl)-2-propen-1-one (501 mg, 1.27 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 8 (865 mg, 84% yield).

$^1$H NMR (CDCl$_3$) δ 1.50-1.7 (m, 2H), 2.00-2.20 (t, 2H), 2.60-2.80 (m, 8H), 3.20 (s, 2H) 3.90 (s, 3H), 4.10-4.20 (t, 2H), 6.94-6.98 (d, J=5.33, 1H), 7.20-7.60 (m, 12H), 7.70-7.80 (d, 1H J=5.33, Hz), 8.10-8.15 (t, 1H) 8.80-8.85 (d, 1H J=5.33 Hz), 12.40 (s, 1H); FABMS: 704 (M+H).

Example 6

N1-[4-chloro-2-(2-chlorobenzoyl)phenyl]-2-(4-3-I(4-oxo-3-phenyl-4H-2-chromenyl)oxy]propylpiperazino)acetamide (8a)

To a compound of N1-[4-chloro-2-(2-chlorobenzoyl)phenyl]-2-piperazino acetamide (500 mg, 1.46 mmol) in dry acetone (20 mL) was added anhydrous potassium carbonate (1 g, 7.30 mmol) and 3-(3-bromopropoxy)-2-phenyl-4H-4-chromenone (524 mg, 1.46 mmol). The reaction mixture was refluxed for 24 h and the reaction was monitored by TLC using ethyl acetate-hexane (6:4) as a-solvent system. The potassium carbonate was then removed by suction filtration and the solvent was evaporated under vacuum to afford the crude product. This was further purified by column chromatography using ethyl acetate:hexane (6:4) as a solvent system to obtain the pure product (786 mg, 79% yield).

¹H NMR (CDCl₃) δ 1:58-1.72 (m, 2H), 2.42-2.48 (t, 2H) 2.55-2.65 (m, 4H)1 2.75-2.82 (m, 4H), 3.20 (s, 2H)1 3.85-3.90 (t, 2H), 6.85-6.98 (d, 1H J=9.06 Hz), 7.40-7.80 (m, 12H) 8.20-8.35 (m, 2H)1 8.40-8.45 (d, 1H J=7.33, Hz), 12.40 (s, 1H); FABMS: 670 (M+H).

Example 7

N1-[4-chloro-2-(2-chlorobenzoyl)phenyl]-2-(4-[2-tert-butyl)imidazo[1,2-a]pyridine-8-yl]carbonylpiperazino) acetamide (6e)

To a compound of N1-[4-chloro-2-(2-chlorobenzoyl)phenyl]-2-chloroacetamide (500 mg, 1.27 mmol] in dry acetone (20 mL) was added anhydrous potassium carbonate (876 mg, 6.35 mmol) and -(tert-butyl) imidazo[1,2-a]pyridine-8-carbonyl chloride (310 mg, 1.27 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 6e (650 mg, 86% yield).

¹H NMR (CDCl₃) δ 1.30 (9, 2H), 2.80-2.90 (m, 4H), 3.30 (s, 2H)1 3.50-3.60 (m, 4H), 6.70-6.75 (t, 1H)1 7.20-7.60, (m, 8) 8.05-8.10 (d, 1H J=9.06, Hz), 8.85-8.90 (d, 1H J=7.93, Hz), 12.30 (s, 1H); FABMS: 592 (M+H).

Example 8

N1-[4-chloro-2-(2-chlorobenzoyl)phenyl]-2-(4-2-[4-chloro-2-(2-chlorobenzoyl)anilino]-2-oxoethylpiperazino)acetamide (6f)

To a compound of N1-[4-chloro-2-(2-chlorobenzoyl)phenyl]-2-piperazinoacetamide (500 mg, 1.46 mmol] in dry acetone (20 mL) was added anhydrous potassium carbonate (880 g, 6.37 mmol) and N1-[4-chloro-2-(2-chlorobenzoyl) phenyl]-2-chloroacetamide (434 mg, 1.46 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 6f (768 mg, 86% yield).

1H NMR (CDCl₃) 2.60 (s, 4H), 3.10-3.15 (m, 4H), 3.20-3.28 (m, 4H), 7.20-7.42 (m, 12H), 8.80-8.84 (d, 2H J=9-06 Hz), 12.40 (s, 1H); FABMS: 698 (M+H).

Example 9

[2-(4-4-[4-(2-benzoyl-4-chlorophenoxy)butyl]piperazinobutoxy)-5-chlorophenyl(Phenyl)methanone (8b)

To a compound of [2-(4-bromobutoxy)-5-chlorophenyl] (phenyl)methanone (500 mg, 1.36 mmol) in dry acetone (20 mL) was added anhydrous potassium carbonate (940 mg, 6.81 mmol) and piperazine (58 mg, 0.68 mmol). The reaction mixture was refluxed for 12 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product 8b (750 mg, 84% yield).

¹H NMR (CDCl₃) δ 1.30-1.40 (m, 4H)1 1.44-1.60 (m, 4H), 2.20-2.35 (m, 4H), 2.40-2.65 (m, 8H), 3.80-4.00 (m, 4H), 6.80-7.00 (d, 2H J=9.06, Hz), 7.30-7.65 (m, 12H), 7.70-7.70 (d, 2H J=9.06, Hz); FABMS: 659 (M+H).

Example 10

N1-[4-chloro-2-(2-chlorobenzoyl)phenyl]-2-4-[3-(4-2-[4-chloro-2-(2-chloro benzoyl anilino]-2-oxoethylpiperazino)propyl]piperazino acetamide (6g)

To a compound of N1-[4-chloro-2-(2-chlorobenzoyl)phenyl]-2-piperazinoacetamide (500 mg, 1.27 mmol) in dry acetone (20 mL) was added anhydrous potassium carbonate (876 mg, 6.35 mmol) and 1,3-dibromo propane (128 mg, 0.63 mmol). The reaction mixture was refluxed for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using -ethyl acetate:hexane (6:4) as a solvent system to obtain the pure product (610 mg, 78% yield).

¹H NMR (CDCl₃) δ 1.50-1.62 (m, 2H), 2.50-2.56 (t, 4H), 2.60-2.75 (m, 8H), 2.80-2.95, (m, 8H) 3.20 (s, 4H), 7.30-7.60, (m, 12) 8.78-8.82 (d, 2H J=5.33, Hz), 12.30 (s, 2H); FABMS: 824 (M+H).

Thermal Denaturation Studies

Compounds were subjected to thermal denaturation studies with duplex-form calf thymus DNA (CT-DNA). Working solutions in aqueous buffer (10 mM NaH2PO4/Na2HPO4, 1 mM Na2EDTA, pH 7.00+0.01) containing CT-DNA (100 µm in phosphate) and the BPD (20 µm) were prepared by addition of concentrated BPD solutions in DMSO to obtain a fixed [BPD]/[DNA] molar ratio of 1:5. The DNA-BPD solutions were incubated at 37° C. for 0, 18, and 36 h prior to analysis. Samples were monitored at 260 nm using a Beckman DU-7400 spectrophotometer fitted with high performance temperature controller, and heating was applied at 1° C. min-1 in the 40-90° C. range. DNA helix coil transition temperatures (Tm) were obtained from the maxima in the (dA260)/dT derivative plots. Results are given as the mean±standard deviation from three determinations and are corrected for the effects of DMSO co-solvent using a linear correction term. Drug-induced alterations in DNA melting behavior are given by: ΔTm=Tm(DNA+BPD)−Tm(DNA alone), where the Tm value for the BPD-free CT-DNA is 69.0±0.01. The fixed [BPD]/[DNA] ratio used did not result in binding saturation of the host DNA duplex for any compound examined. Compound 6a, 6b, 6c, 6d, 6e, 6f, 6g, 8, 8a and 8b at 0 hr, 18 hr and 36 hr gradually increased at 37° C.

TABLE 1

Thermal denaturation data of Benzophenone hybrids with calf thymus (CT) DNA

| Compounds | [BPD]:[DNA] molar ratio[b] | $\Delta T_m$ (° C.)[a] after incubation at 37° C. for | | |
|---|---|---|---|---|
| | | 0 h | 18 h | 36 h |
| 6a | 1:5 | 1.2 | 1.7 | 2.2 |
| 6b | 1:5 | 1.5 | 2.1 | 2.6 |
| 6c | 1:5 | 1.4 | 1.6 | 2.3 |
| 6d | 1:5 | 1.5 | 1.9 | 2.7 |
| 6e | 1:5 | 1.9 | 2.3 | 2.8 |
| 6f | 1:5 | 1.3 | 2.1 | 3.0 |
| 6g | 1:5 | 1.6 | 2.6 | 2.9 |
| 8 | 1:5 | 1.5 | 2.3 | 2.4 |
| 8a | 1:5 | 1.4 | 2.1 | 2.1 |
| 8b | 1:5 | 1.6 | 2.6 | 2.9 |
| DC-81 | 1:5 | | 0.3 | 0.7 |

[a]For CT-DNA alone at pH 7.00 ± 0.01, $T_m$ = 69.6° C. ± 0.01 (mean value from 10 separate determinations), all $\Delta T_m$ values are ± 0.1-0.2° C.
[b]For a 1:5 molar ratio of [ligand]/[DNA], where CT-DNA concentration = 100 µM and ligand concentration = 20 µM in aqueous sodium phosphate buffer [10 mM sodium phosphate + 1 mM EDTA, pH 7.00 ± 0.01].
BPD = benzophenone derivatives Biological Activity: some of in vitro biological activity studies were carried out at the National Cancer Institute, Maryland, USA.

Compounds described herein were evaluated for in vitro anticancer activity. Particularly the 6a, 6b, 6d, 6h, 8a and 8b compounds were evaluated for in vitro anticancer activity against sixty human tumor cells derived from nine cancer types (leukemia, non-small-cell lung, colon, CNS1 melanoma, ovarian, prostate, and breast cancer) as shown in (Table 2 and 3). For the compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of log 10 TGI and log 10 LC50 as well as log 10 GI50 for 6d and 8a is listed in Table 2 and 3. As demonstrated by mean graph pattern, compound 6d, 8a and 8b exhibited an interesting profile of activity and selectivity for various cell lines. The mean graph mid point of log 10 TGI and log 10 LC50 showed similar pattern to the log 10 GI50 mean graph mid points.

TABLE 2

$Log_{10}$ GI50 $log_{10}$TGI and $log_{10}$LC50 mean graphs midpoints (MG_MID) of in vitro cytotoxicity data for the representative compounds against human tumor cell lines

| Compound | $Log_{10}$GI50 | $Log_{10}$TGI | $Log_{10}$LC50 |
|---|---|---|---|
| 6a | −6.51 | −6.54 | −4.35 |
| 6b | −6.57 | −6.89 | −5.73 |
| 6d | −6.82 | −6.56 | −4.62 |
| 6e | −5.93 | −6.28 | −5.39 |
| 8a | −6.19 | −6.33 | −5.32 |
| 8b | −6.35 | −5.51 | −5.25 |

TABLE 3

Log $GI_{50}$ (concentration in mol/L causing 50% growth inhibition) values for benzophenone hybrids

| Cancer | Compound (6a) | Compound (6b) | Compound (6d) | Compound (6e)) | Compound (8a) | Compound (8b) |
|---|---|---|---|---|---|---|
| Leukemia | −5.45 | −5.26 | −6.82 | −6.07 | −6.11 | −6.20 |
| Nonsmall-cell-lung | −5.60 | −5.44 | −6.41 | −6.18 | −5.75 | −5.49 |
| Colon | −5.24 | −5.67 | −6.64 | −6.23 | −5.75 | −.6.47 |
| CNS | −5.25 | −5.23 | −6.65 | −5.85 | −5.69 | −5.38 |
| Melanoma | −5.89 | −5.75 | −6.69 | −5.46 | −5.79 | −.5.70 |
| Ovarian | −5.17 | −5.24 | −6.66 | −5.45 | −5.80 | −5.24 |
| Renal | −5.81 | −5.25 | −6.67 | −5.98 | −5.71 | −5.59 |
| Prostate | −5.75 | −4.78 | −6.40 | −5.87 | −5.56 | −5.50 |
| Breast | −5.41 | −5.17 | −6.75 | −5.67 | −5.70 | −5.46 |

Each cancer type represents the average of six to nine different cancer cell lines.

In vitro evaluation of cytotoxic activity. Compounds 6a, 6b, 6d, 6e, 8a and 8b were evaluated for in vitro anticancer activity against nine human tumor cells derived from six cancer types (colon, prostate, oral, lung, cervix and breast cancer) as shown in Table 2. Compounds 6a, 6c, 6d 6e and 8a showed promising cytotoxicity against some cancer cell lines (Table 2). Compounds 6a, 6b, 6d, 6e, 8a and 8b have been evaluated for their in vitro cytotoxicity in selected human cancer cell lines of colon (Colo205), lung (Hop-62), cervix (SiHa), prostate (DU145, PC3), oral (DWD, HT1080), and breast (MCF7, Zr-75-1) origin. A protocol of 48 h continuous drug exposure has been used and an Adriamycin (ADR) protein assay has been used to estimate cell viability or growth. The results are expressed as percent of cell growth determined relative to that of untreated control cells Among them 6a, 6d, 8a and 8b, exhibit a wide spectrum of activity against sixty cell lines in nine cell panels, with GI50 value of <20 nM. In the non-small cell lung cancer panel, the growth of HOP-62, NCI-H23 cell lines were affected by compound 6d with G150 values as 11.7, 13.9 and 17.2 nM respectively. The GI50 values of compound 6d against colon cancer HCC-2988, HCT-116 and KM12 cell lines are 11.6, 11.2 and 11.4 nM respectively. The GI50 values for compound 6d against CNS SF-295, SF-539, SNB-19 and SNB-75 cell lines are in a range of 11.6-24.2 nM. Four cancer cell lines (OVCAR-4, OVCAR-5, OVCAR-8 and SK-OV-3) in the ovarian cancer cell panel were affected by compound 6d with GI50 values of 30.6, 14.9, 30.5 and 78.6 nM respectively. In this study compound 6d exhibited cytotoxicity activity against renal and breast cancer panels with GI5o values (11.6-43.4 nM), compound 8a exhibits activity against fifty-five cell lines in nine cancer cell panels with GI50 values of <10 mM. Compound 8a exhibits activity against fifty-seven cell lines in nine cancer cell panels, $GI_{50}$ values of <10 mM. In vitro cytotoxicity of compounds 6d, 8a, and 8b in selected cancer cell lines has been illustrated in Table 3. The average G150 values for each cancer panel of compounds 6a, 6b, 6d, 6e, 8a and 8b have been illustrated in Table 2.

Exemplary embodiments disclosed herein include a benzophenone hybrid of the formula

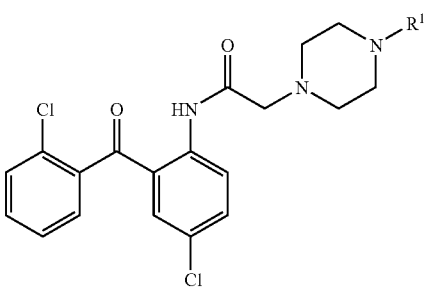

wherein R1 is elected from the group consisting of pyridyl, pyrimidyl, 2-methoxy piperazine, 4-chloroquinazoline, 2-(tert-butyl)imidazo[1,2-a]pyridine-8-carbonyl, N1-[4-chloro-2-(2-chlorobenzoyl)phenyl]-2-chloro tacetamide, 1,3-dibromo propane and butyl chalcone and wherein the benzophene hybrid is effective as an anti-cancer agent.

Exemplary embodiments disclosed herein also include benzophenone hybrids with one of the following non-limiting structures:

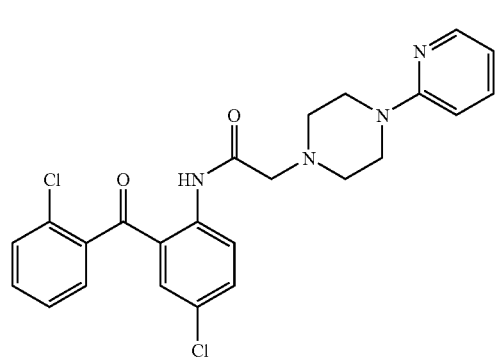

6a

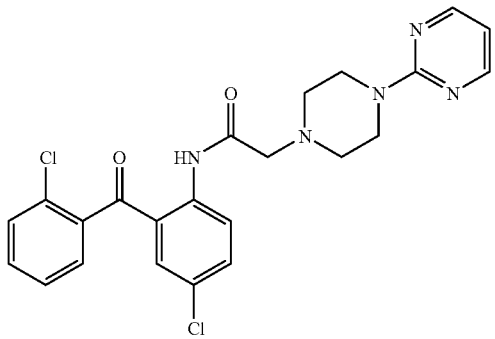

6b

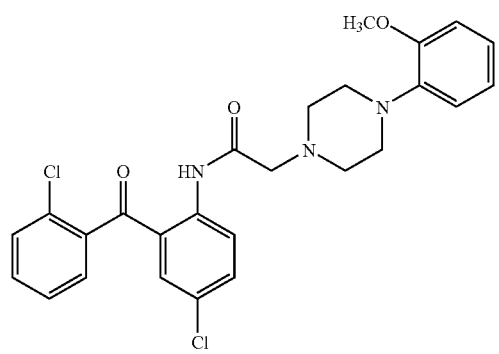

6c

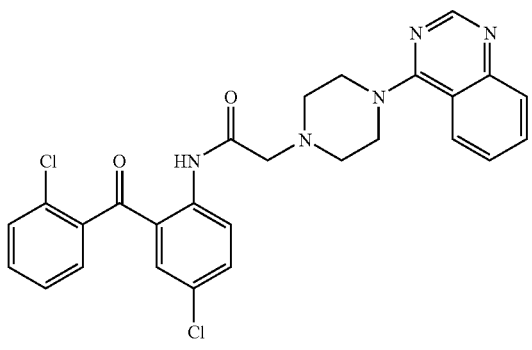

6d

-continued
6e
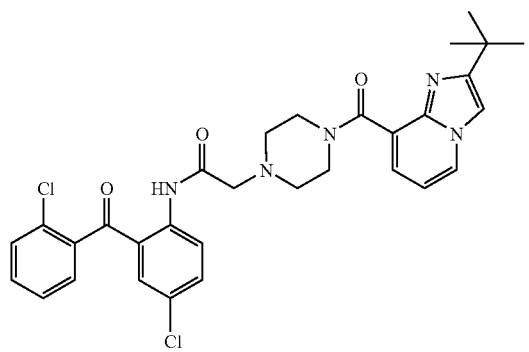
6f
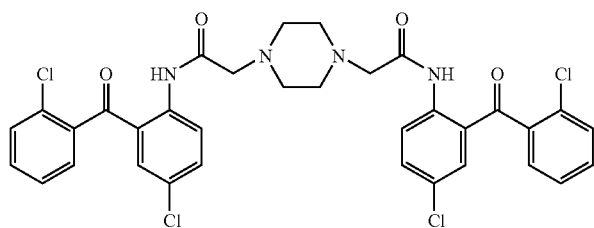
6g
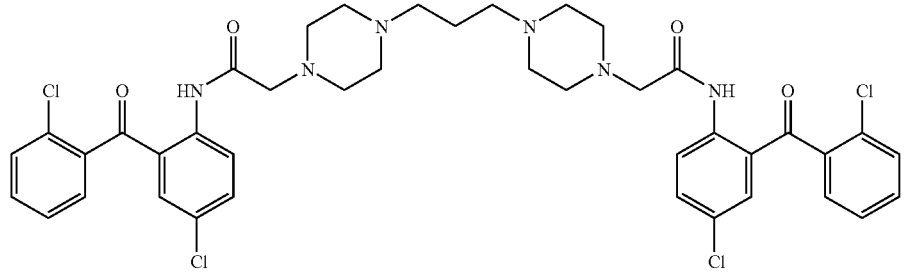
6h
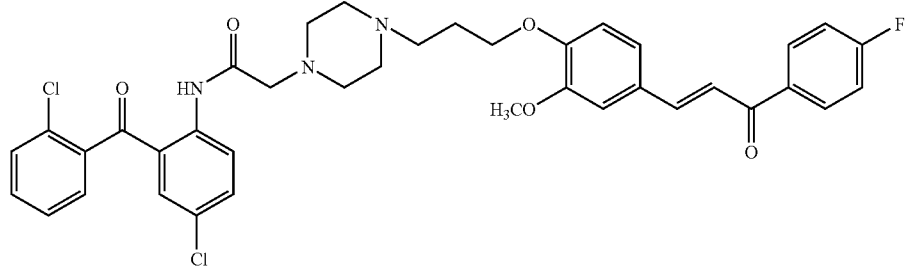
8a
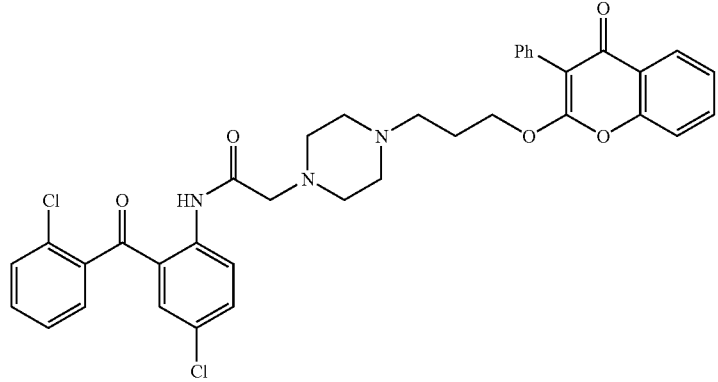
8b
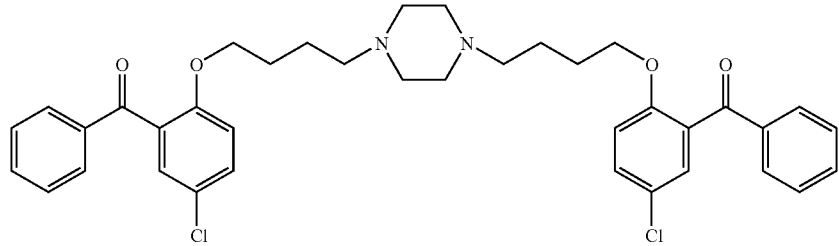

Exemplary embodiments disclosed herein also include benzophenone hybrids that exhibit in vitro anticancer activity against a human cancer.

Exemplary embodiments disclosed herein also include benzophenone hybrids wherein the human cancer is one or more of leukemia, melanoma, colon cancer, prostate cancer, ovarian cancer, lung cancer, renal cancer, central nervous system cancer, and breast cancer.

Exemplary embodiments disclosed herein also include benzophenone hybrids wherein the hybrid exhibits 50% cell growth inhibition against a human cancer in the range of about −5.5 to about −7.0.

Exemplary embodiments disclosed herein also include benzophenone hybrids wherein the hybrid exhibits total cell growth inhibition against a human cancer in the range of about −5.5 to about −7.0.

Exemplary embodiments disclosed herein also include benzophenone hybrids wherein the hybrid exhibits 50% cell death against a human cancer in the range of about −4.0 to about −5.5.

Exemplary embodiments disclosed herein also include processes for forming benzophenone hybrids including, without limitation, a process for the preparation of a benzophenone hybrid of the formula

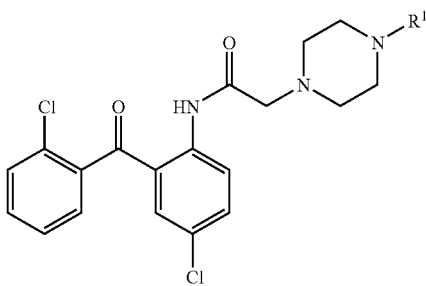

wherein R1 is elected from the group consisting of pyridyl, pyrimidyl, 2-methoxy piperazine, 4-chloroquinazoline, 2-(tert-butyl)imidazo[1,2-a]pyridine-8-carbonyl, N1-[4-chloro-2-(2-chlorobenzoyl)phenyl]-2-chloro acetamide, 1,3-dibromo propane and butyl chalcone wherein the process comprises the steps of:

a) preparing a N1-[4-chloro-2-(2-chlorobenzoyl)phenyl]-2-chloroacetamide compound of formula 5 from a compound of formula 1,

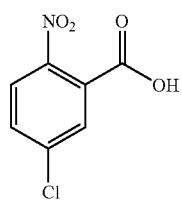

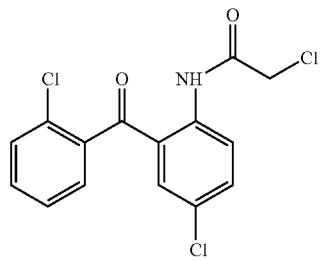

b) reacting the above the N1-[4-chloro-2-(2-chloro benzoyl)phenyl]-2-chloroacetamide compound of formula 5 with anhydrous potassium carbonate and a reagent selected from the group consisting of (i) 1-(2-pyridyl)piperazine, (ii) 1-(2-pyrimidinyl)piperazine, (iii) 1-(2-methoxyphenyl)piperazine, (iv) 4-piperazinoquinazoline, (v) (tert-butyl)imidazo[1,2-a]pyridine-8-carbonyl chloride, (vi) N1-[4-chloro-2-(2-chlorobenzoyl)phenyl]-2-chloroacetamide, and (vii) N1-[4-chloro-2-(2-chlorobenzoyl)phenyl]-2-piperazinoacetamide in acetone, under reflux, for a period of about 20 to about 30 hrs, followed by the removal of potassium carbonate by filtration and evaporating the solvent, under vacuum, and purifying the resultant product to obtain a benzophenone hybrid, c) reacting the above the N1-[4-chloro-2-(2-chloro benzoyl)phenyl]-2-chloroacetamide compound of formula 5 with Boc-piperazine in acetone under reflux for a period of about 15 to about 20 hrs, followed by the evaporation of solvent to obtain the compound of formula:

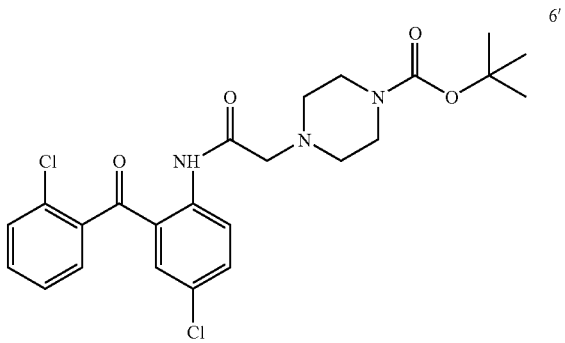 [SMILES: CC(C)(C)OC(=O)N1CCN(CC(=O)Nc2ccc(Cl)cc2C(=O)c2ccccc2Cl)CC1]

d) reacting the above the compound obtained in step (c) with trifluoroacetic acid in dichloromethane at a temperature of about 20 to about 30° C., followed by the evaporation of solvent to obtain the compound of formula:

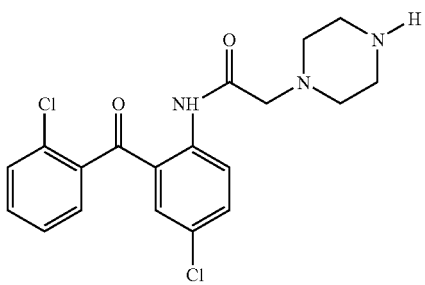

e) reacting the above the N1-[4-chloro-2-(2-chlorobenzoyl)phenyl]-2-piperazinoacetamide compound with (E)-3-[4-(3-bromopropoxy)-3-methoxyphenyl]-1-(4-luorophenyl)-2-propen-1-one or 3-(3-bromopropoxy)-2-phenyl-4H-4-chromenone in acetone in the presence potassium carbonate, under reflux, for a period of about 15 to about 20 hrs, followed by the removal of potassium carbonate by alteration and evaporating the solvent, under vacuum, and purifying the resultant product to obtain N1-[4-chloro-2-(2-chlorobenzoyl)phenyl]-2-[4-(4-4-[(E)-3-(4-fluorophenyl)-3-oxo-1-propenyl]-2-methoxyphenoxy butyl)piperazino]acetamide or N1-[4-chloro-2-(2-chlorobenzoyl)phenyl]-2-(4-3-[(4-oxo-3-phenyl-4H-2-chromenyl)oxy]propylpiperazino)acetamide.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A benzophenone hybrid of the formula

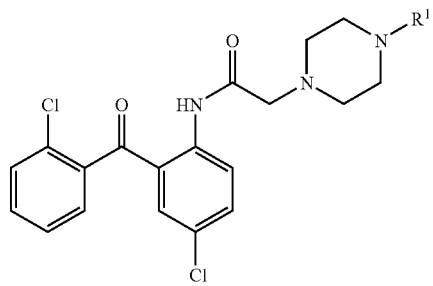

wherein the benzophenone hybrids are selected from the group consisting of

N1-[4-chloro-2-(2-chlorobenzoyl)phenyl]-2-(4-2-[4-chloro-2-(2-chlorobenzoyl)anilino]-2-oxoethylpiperazino)acetamide (6f);

N1-[4-chloro-2-(2-chlorobenzoyl)phenyl]-2-4-[3-(4-2-[4-chloro-2-(2-chlorobenzoyl) anilino]-2-oxoethylpiperazino)propyl]piperazino)acetamide (6g);

N1-[4-chloro-2-(2-chlorobenzoyl)phenyl]-2-[4-(4-4-[(E)-3-(4-fluorophenyl)-3-oxo-1-propenyl]-2-methoxyphenoxybutyl)piperazino]acetamide (6h); and N1-[4-chloro-2-(2-chlorobenzoyl)phenyl]-2-(4-3-[(4-oxo-3-phenyl-4-H-2-chromenyl)oxy]propylpiperazino)acetamide (8a) or wherein R1 is selected from the group consisting of pyridyl, pyrimidyl, 2-(tert-butyl)imidazo[1,2-a]pyridine-8-carbonyl, 2-methoxy phenyl and quinazolinyl.

2. A benzophenone hybrid according to claim 1 wherein the structure of the hybrid is one or more of:
   N1-[4-chloro-2-(2-chlorobenzoyl)phenyl]-2-[4-(2-pyridyl) piperazino]acetamide (6a);
   N1-[4-chloro-2-(2-chlorobenzoyl)phenyl]-2-[4-(2-pyrimidinyl)piperazino]acetamide 6b);
   N1-[4-chloro-2-(2-chlorobenzoyl)phenyl]-2-[4-[(2-methoxyphenyl)piperazino]acetamide (6c);
   N1-4-chloro-2-(2-chlorobenzoyl)phenyl]-2-[4-(4-quinazolinyl)piperazino]acetamide (6d); and
   N1-[4-chloro-2-(2-chlorobenzoyl)phenyl]-2-(4-[2-(tert-butyl)imidazo[1,2-a]pyridin-8-yl]carbonylpiperazino) acetamide (6e).

3. A benzophenone hybrid according to claim 1 wherein the hybrid exhibits in vitro anticancer activity against a human cancer.

4. A benzophenone hybrid according to claim 3 wherein the human cancer is one or more of leukemia, melanoma, colon cancer, prostate cancer, ovarian cancer, lung cancer, renal cancer, central nervous system cancer, and breast cancer.

5. A benzophenone hybrid according to claim 1 wherein the hybrid exhibits 50% cell growth inhibition against a human cancer in the range of about −5.5 to about −7.0.

6. A benzophenone hybrid according to claim 1 wherein the hybrid exhibits total cell growth inhibition against a human cancer in the range of about −5.5 to about −7.0.

7. A benzophenone hybrid according to claim 1 wherein the hybrid exhibits 50% cell death against a human cancer in the range of about −4.0 to about −5.5.

8. A process for the preparation of a benzophenone hybrid of the formula

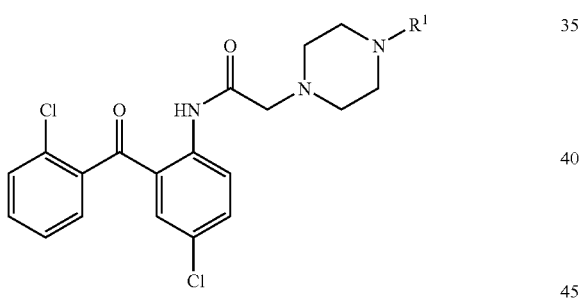

wherein the benzophenone hybrids are selected from the group consisting of
   N1-[4-chloro-2-(2-chlorobenzoyl)phenyl]-2-(4-2-[4-chloro-2-(2-chlorobenzoyl)anilino]-2-oxoethylpiperazino)acetamide (6f);
   N1-[4-chloro-2-(2-chlorobenzoyl)phenyl]-2-4-[3-(4-2-[4-chloro-2-(2-chlorobenzoyl) anilino]-2-oxoethylpiperazino)propyl]piperazino)acetamide (6g);
   N1-[4-chloro-2-(2-chlorobenzoyl)phenyl]-2-[4-(4-4-[(E)-3-(4-fluorophenyl)-3-oxo-1-propenyl]-2-methoxyphenoxybutyl)piperazino]acetamide (6h); and
   N1-[4-chloro-2-(2-chlorobenzoyl)phenyl]-2-(4-3-[(4-oxo-3-phenyl-4-H-2-chromenyl)oxy]propylpiperazino)acetamide (8a) or
   wherein R1 is selected from the group consisting of pyridyl, pyrimidyl, 2-(tert-butyl)imidazo[1,2-a]pyridine-8-carbonyl, 2-methoxy phenyl and quinazolinyl
   wherein the process comprises the steps of:
   a) preparing a N1-[4-chloro-2-(2-chlorobenzoyl)phenyl]-2-chloroacetamide compound of formula 5 from a compound of formula 1,

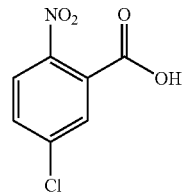

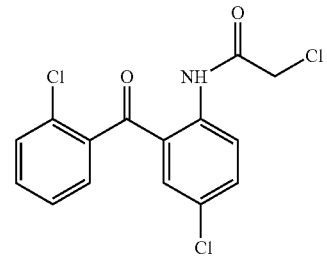

b) reacting the above the N1-[4-chloro-2-(2-chloro benzoyl)phenyl]-2-chloroacetamide compound of formula 5 with anhydrous potassium carbonate and a reagent selected from the group consisting of
   (i) 1-(2-pyridyl)piperazine,
   (ii) 1-(2-pyrimidinyl)piperazine,
   (iii) 1-(2-methoxyphenyl)piperazine,
   (iv) 4-piperazinoquinazoline,
   (v) (tert-butyl) imidazo[1,2-a]pyridine-8-carbonyl chloride,
   (vi) N1-[4-chloro-2-(2-chlorobenzoyl)phenyl]-2-chloroacetamide, and
   (vii) N1-[4-chloro-2-(2-chlorobenzoyl)phenyl]-2-piperazinoacetamide in acetone, under reflux, for a period of about 20 to about 30 hrs, followed by the removal of potassium carbonate by filtration and evaporating the solvent, under vacuum, and purifying the resultant product to obtain a benzophenone hybrid, c) reacting the above the N1-[4-chloro-2-(2-chloro benzoyl)phenyl]-2-chloroacetamide compound of formula 5 with Boc-piperazine in acetone under reflux for a period of about 15 to about 20 hrs, followed by the evaporation of solvent to obtain the compound of formula:

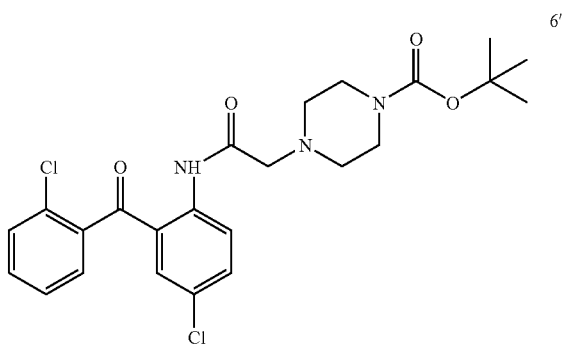 [SMILES: CC(C)(C)OC(=O)N1CCN(CC(=O)Nc2ccc(Cl)cc2C(=O)c2ccccc2Cl)CC1]

d) reacting the above the compound obtained in step (c) with trifluoroacetic acid in dichloromethane at a temperature of about 20 to about 30° C., followed by the evaporation of solvent to obtain the compound of formula:

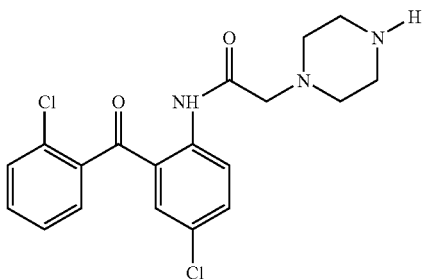

e) reacting the above the N1-[4-chloro-2-(2-chlorobenzoyl)phenyl]-2-piperazinoacetamide compound with (E)-3-[4-(3-bromopropoxy)-3-methoxyphenyl]-1-(4-fluorophenyl)-2-propen-1-one or 3-(3-bromopropoxy)-2-phenyl-4H-4-chromenone in acetone in the presence potassium carbonate, under reflux, for a period of about 15 to about 20 hrs, followed by the removal of potassium carbonate by alteration and evaporating the solvent, under vacuum, and purifying the resultant product to obtain N1-[4-chloro-2-(2-chlorobenzoyl)phenyl]-2-[4-(4-4-[(E)-3-(4-fluorophenyl)-3-oxo-1-propenyl]-2-methoxyphenoxy butyl)piperazino]acetamide or N1-[4-chloro-2-(2-chlorobenzoyl) phenyl]-2-(4-3-[(4-oxo-3-phenyl-4H-2-chromenyl)oxy]propylpiperazino)acetamide.

9. The process of claim 8 wherein the compounds of the benzophenone hybrid of formula A are:

N1-[4-chloro-2-(2-chlorobenzoyl)phenyl]-2-[4-(2-pyridyl) piperazino]acetamide (6a);

N1-[4-chloro-2-(2-chlorobenzoyl)phenyl]-2-[4-(2-pyrimidinyl)piperazino]acetamide (6b);

N1-[4-chloro-2-(2-chlorobenzoyl)phenyl]-2-[4-[(2-methoxyphenyl)piperazino]acetamide (6c);

N1-4-chloro-2-(2-chlorobenzoyl)phenyl]-2-[4-(4-quinazolinyl)piperazino]acetamide (6d); or N1-[4-chloro-2-(2-chlorobenzoyl)phenyl]-2-(4-[2-(tert-butyl)imidazo[1,2-a]pyridin-8-yl]carbonylpiperazino) acetamide (6e).

* * * * *